(12) United States Patent
Jacquin et al.

(10) Patent No.: US 10,321,840 B2
(45) Date of Patent: Jun. 18, 2019

(54) DEVELOPMENT OF FULLY-AUTOMATED CLASSIFIER BUILDERS FOR NEURODIAGNOSTIC APPLICATIONS

(75) Inventors: Arnaud Jacquin, New York, NY (US); Asmir Vodencarevic, Tuzla (BA)

(73) Assignee: Brainscope Company, Inc., Bethesda, MD (US)

( * ) Notice: Subject to any disclaimer, the term of this patent is extended or adjusted under 35 U.S.C. 154(b) by 994 days.

(21) Appl. No.: 12/541,272

(22) Filed: Aug. 14, 2009

(65) Prior Publication Data

US 2011/0038515 A1 Feb. 17, 2011

(51) Int. Cl.
*G06K 9/62* (2006.01)
*G16H 50/20* (2018.01)
*A61B 5/00* (2006.01)
*A61B 5/16* (2006.01)
*A61B 5/0476* (2006.01)

(52) U.S. Cl.
CPC .............. *A61B 5/0476* (2013.01); *A61B 5/16* (2013.01); *A61B 5/7264* (2013.01); *G06K 9/6229* (2013.01); *A61B 5/726* (2013.01); *A61B 5/7207* (2013.01); *A61B 5/7267* (2013.01); *G16H 50/20* (2018.01)

(58) Field of Classification Search
CPC ....... A61B 5/0476; A61B 5/16; A61B 5/7264; A61B 5/726; A61B 5/7267; A61B 5/7207; G06K 9/6229; G06F 19/345
USPC ................................. 600/544, 545
See application file for complete search history.

(56) References Cited

U.S. PATENT DOCUMENTS 4,188,956 A 2/1980 John
4,421,122 A 12/1983 Duffy
4,913,160 A 4/1990 John
(Continued)

FOREIGN PATENT DOCUMENTS

EP 1 275 340 A1 1/2003
WO WO 91/09372 A1 6/1991
(Continued)

OTHER PUBLICATIONS

Skalak, "Prototype and Feature Selection by Sampling and Random Mutation Hill Climbing Algorithms.", Proceedings of the Eleventh International Conference on Machine Learning, pp. 293-301, New Brunswick, New Jersey, 1994.*
(Continued)

*Primary Examiner* — Tiffany Weston
*Assistant Examiner* — Tho Q Tran
(74) *Attorney, Agent, or Firm* — Finnegan, Henderson, Farabow, Garrett & Dunner, L.L.P.

(57) ABSTRACT

Methods for constructing classifiers for binary classification of quantitative brain electrical activity data is described. The classifier building methods are based on the application of one or more evolutionary algorithms. In one embodiment, the evolutionary algorithm used is a genetic algorithm. In another embodiment, the evolutionary algorithm used is a modified Random Mutation Hill Climbing algorithm. In yet another embodiment, a combination of a genetic algorithm and a modified Random Mutation Hill Climbing algorithm is used for building a classifier. The classifier building methods are fully automated, and are adapted to generate classifiers (for example, Linear Discriminant Functions) with high sensitivity, specificity and classification accuracy.

21 Claims, 5 Drawing Sheets

(56) References Cited

U.S. PATENT DOCUMENTS

| | | | |
|---|---|---|---|
| 5,390,282 A * | 2/1995 | Koza et al. .................... 706/13 |
| 6,360,122 B1 | 3/2002 | Fischell et al. |
| 6,360,191 B1 * | 3/2002 | Koza et al. ...................... 703/6 |
| 6,556,951 B1 * | 4/2003 | Deleo et al. ................. 702/183 |
| 6,654,623 B1 | 11/2003 | Kästle |
| 6,658,287 B1 * | 12/2003 | Litt et al. ..................... 600/544 |
| 6,757,558 B2 | 6/2004 | Lange et al. |
| 7,054,453 B2 | 5/2006 | Causevic et al. |
| 7,089,927 B2 | 8/2006 | John et al. |
| 7,299,088 B1 | 11/2007 | Thakor et al. |
| 7,302,064 B2 | 11/2007 | Causevic et al. |
| 7,318,051 B2 * | 1/2008 | Weston ............... G06K 9/6215 706/12 |
| 7,373,198 B2 | 5/2008 | Bibian et al. |
| 7,647,098 B2 | 1/2010 | Prichep |
| 2002/0039455 A1 | 4/2002 | Kanamaru et al. |
| 2002/0183987 A1 * | 12/2002 | Chiang ............................ 703/2 |
| 2003/0088458 A1 * | 5/2003 | Afeyan et al. ................. 705/10 |
| 2003/0154432 A1 * | 8/2003 | Scott et al. .................... 714/724 |
| 2004/0077967 A1 * | 4/2004 | Jordan .......................... 600/544 |
| 2004/0210124 A1 | 10/2004 | Nowinski et al. |
| 2005/0070458 A1 | 3/2005 | John |
| 2005/0100209 A1 * | 5/2005 | Lewis .................. G06K 9/6217 382/159 |
| 2005/0143845 A1 * | 6/2005 | Kaji ............................... 700/28 |
| 2005/0165323 A1 | 7/2005 | Montgomery |
| 2005/0165327 A1 | 7/2005 | Thibault et al. |
| 2006/0004753 A1 | 1/2006 | Coifman et al. |
| 2006/0155751 A1 | 7/2006 | Geshwind et al. |
| 2006/0217632 A1 | 9/2006 | Causevic et al. |
| 2007/0032737 A1 | 2/2007 | Causevic et al. |
| 2007/0100251 A1 | 5/2007 | Prichep |
| 2007/0173732 A1 | 7/2007 | Causevic et al. |
| 2007/0185697 A1 * | 8/2007 | Tan et al. ........................ 703/11 |
| 2007/0208677 A1 * | 9/2007 | Goldberg et al. .............. 706/13 |
| 2008/0091118 A1 * | 4/2008 | Georgopoulos ............. 600/544 |
| 2008/0208073 A1 | 8/2008 | Causevic |
| 2008/0208074 A1 | 8/2008 | Snyder et al. |
| 2008/0249430 A1 | 10/2008 | John et al. |
| 2008/0262371 A1 | 10/2008 | Causevic |
| 2009/0018427 A1 | 1/2009 | Causevic et al. |
| 2009/0082690 A1 | 3/2009 | Phillips |
| 2009/0137924 A1 * | 5/2009 | Kapoor et al. ................ 600/545 |
| 2009/0221930 A1 | 9/2009 | Laken |
| 2009/0247894 A1 | 10/2009 | Causevic |
| 2009/0263034 A1 | 10/2009 | Causevic |
| 2009/0264785 A1 | 10/2009 | Causevic et al. |
| 2009/0264786 A1 | 10/2009 | Jacquin |
| 2010/0041962 A1 | 2/2010 | Causevic et al. |
| 2011/0119212 A1 * | 5/2011 | De Bruin ................. A61B 5/00 706/12 |
| 2011/0218950 A1 * | 9/2011 | Mirowski et al. .............. 706/12 |

FOREIGN PATENT DOCUMENTS

| | | |
|---|---|---|
| WO | WO 2006/034024 | 3/2006 |
| WO | WO 2007/016149 A2 | 2/2007 |
| WO | WO 2007/096452 | 8/2007 |
| WO | WO 2009/063463 A2 | 5/2009 |
| WO | WO 2010/088252 A1 | 8/2010 |

OTHER PUBLICATIONS

Farmer et al., "Large Scale Feature Selection Using Modified Random Hill Mutation Hill Climbing.", Proceedings of the 17th International Conference on Pattern Recognition, p. 1, 2004.*

Bhanu et al., Genetic algorithm based feature selection for target detection in SAR images, 2003, Image and Vision Computing, 21, 591-608.*

U.S. Appl. No. 12/361,174, filed Jan. 28, 2009.

Besserve et al., "Classification methods for ongoing EEG and MEG signals", Bio Res, vol. 40, No. 4, 2007, pp. 415-437.

Blakely, "A fast empirical mode decomposition technique for nonstationary nonlinear time series", Center for Scientific Computation and Mathematical Modeling, University of Maryland, College Park, Oct. 3, 2005.

Coifman et al., "Geometric diffusions as a tool for harmonic analysis and structure definition of data: Multiscale methods," Proceedings of the National Academy of Sciences (PNAS), vol. 102, No. 21, May 24, 2005, pp. 7432-7437.

Coifman et al., "Multiresolution analysis associated to diffusion semigroups: construction and fast algorithms," Tech. Rep. YALE/DCS/TR-1292, Dept. Comp. Sci., Yale University, Jun. 2004, pp. 1-32.

Comon, "Independent component analysis, a new concept?," Signal Processing, 36:287-314 (1994).

Copending U.S. Appl. No. 12/105,439, filed Apr. 18, 2008.

Copending U.S. Appl. No. 12/106,699, filed Apr. 21, 2008.

Copending U.S. Appl. No. 12/576,521, filed Oct. 9, 2009.

Copending U.S. Appl. No. 12/639,357, filed Dec. 16, 2009.

Delorme et al., "Enhanced detection of artifacts in EEG data using higher-order statistics and independent component analysis," NeuroImage 34:1443-1449 (2007).

Hadjileontiadis et al., "Empirical mode decomposition and fractal dimension filter," IEEE Engineering in Medicine and Biology Magazine, Jan./Feb. 2007, p. 30-39.

Higuchi, "Approach to an irregular time series on the basis of the fractal theory," Physica D 31:277-283 (1988).

Hyvarinen, "Fast and robust fixed-point algorithms for independent component analysis," IEEE Transactions on Neural Networks 10(3):626-634 (1999).

John, "Principles of neurometrics", American Journal of EEG Technology, American Society of EEG Technologists, vol. 30, No. 4, Dec. 1, 1990, pp. 251-266.

Jung et al., "Removing electroencephalographic artifacts by blind source separation," Psychophysiology, vol. 37, pp. 163-178, 2000.

Konstam, "Linear discriminant, analysis using genetic algorithms", Applied Computing: States of the Art and Practice—1993. Proceedings of the 1993 ACM/SGAPP Symposium on Applied Computing ACM New York, NY, 1993, pp. 152-156.

Ksiezyk et al., "Neural networks with wavelet preprocessing in EEG artifact recognition," Laboratory of Medical Physics, Institute of Experimental Physics, Warsaw University, Hoza 69 00 681 Warszawa, Poland.

Mahadevan et al., "Valvefunction approximation with diffusion wavelets and laplacian eigenfunctions," University of Massachusetts, Dept. of Computer Science TR-2005-38, and NIPS, accepted, 2005.

Office Action dated Jun. 20, 2011, in U.S. Appl. No. 12/361,174.

PCT International Search Report and the Written Opinion dated Apr. 8, 2010, in related PCT Application No. PCT/US2010/022197.

PCT International Search Report and Written Opinion issued by European Patent Office in International Application No. PCT/US2009/040604, dated Jul. 14, 2009.

PCT International Search Report and Written Opinion dated Dec. 27, 2010, in related PCT/US2010/045290.

PCT International Search Report and Written Opinion dated Dec. 28, 2010, in related PCT/US2010/051621.

PCT International Search Report and Written Opinion dated Jun. 8, 2009, in related PCT/US2009/041109.

PCT International Search Report and Written Opinion dated Mar. 14, 2011, in related PCT/US2010/060170.

Prusseit et al., "Stochastic Qualifiers of Epileptic Brain Function," Phys Rev Lett 98, 138103 (2007).

Vorobyov et al., "Blind noise reduction for multisensory signals using ICA and subspace filtering, with application to EEG analysis," Biol. Cybern. 86, 293-303 (2002).

* cited by examiner

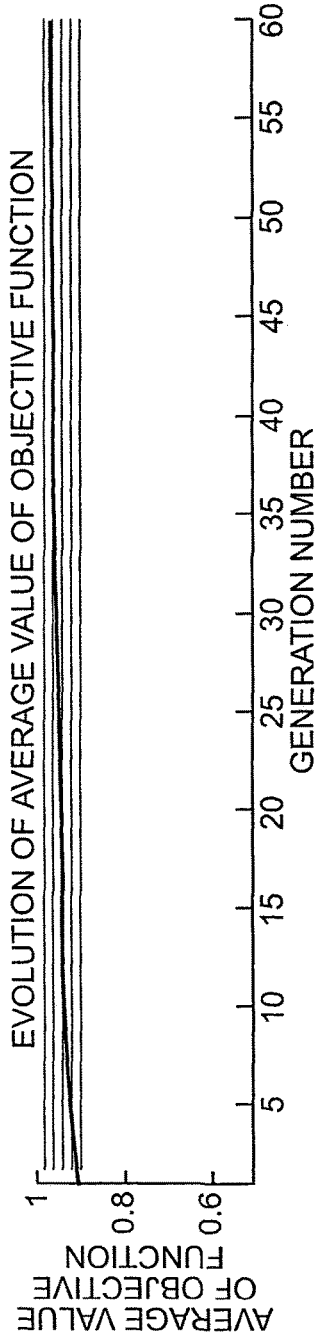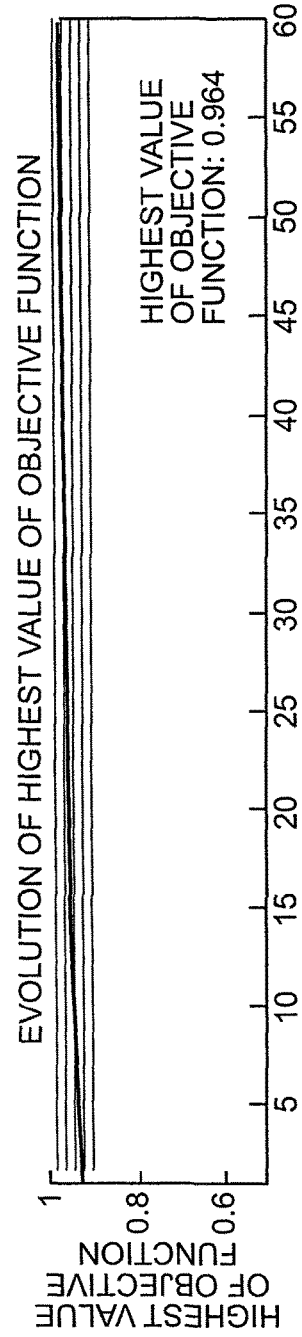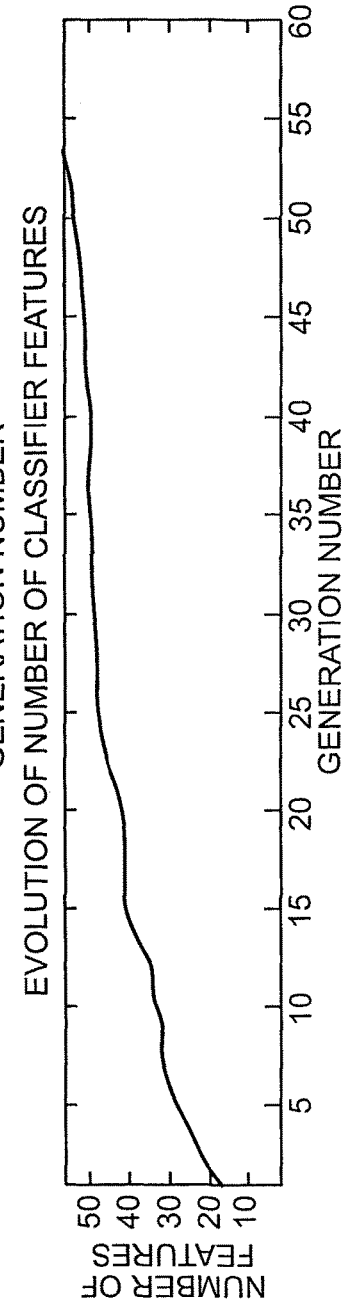

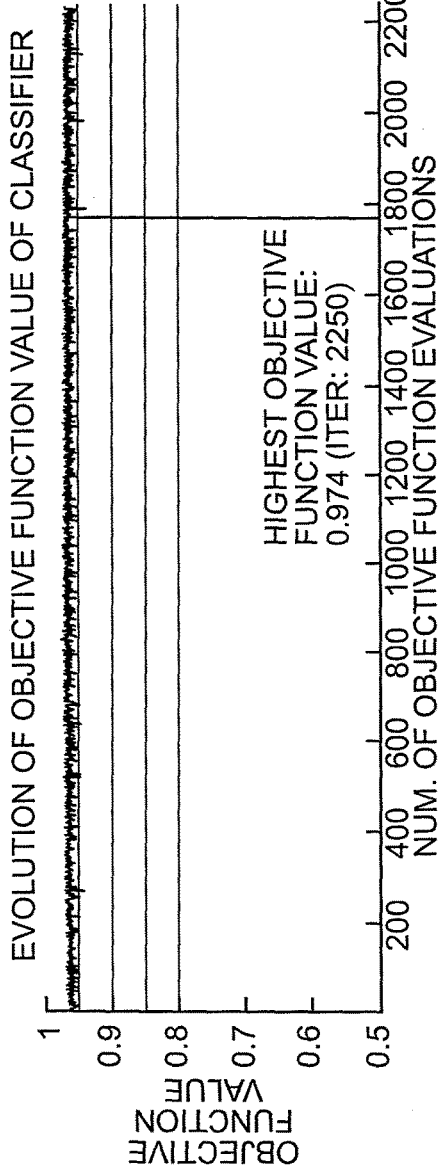
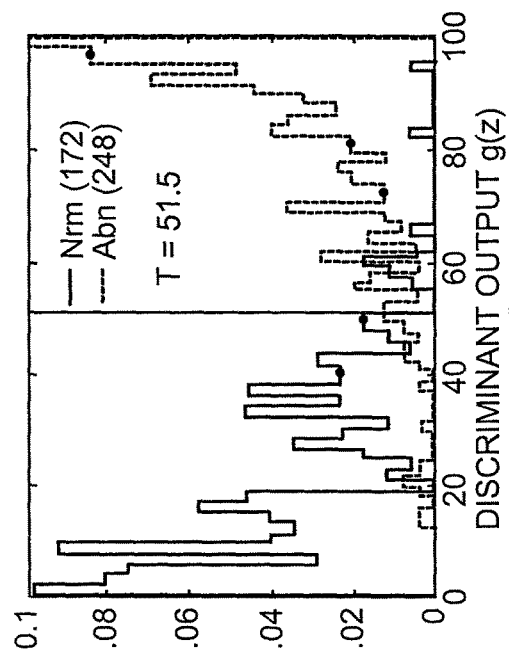
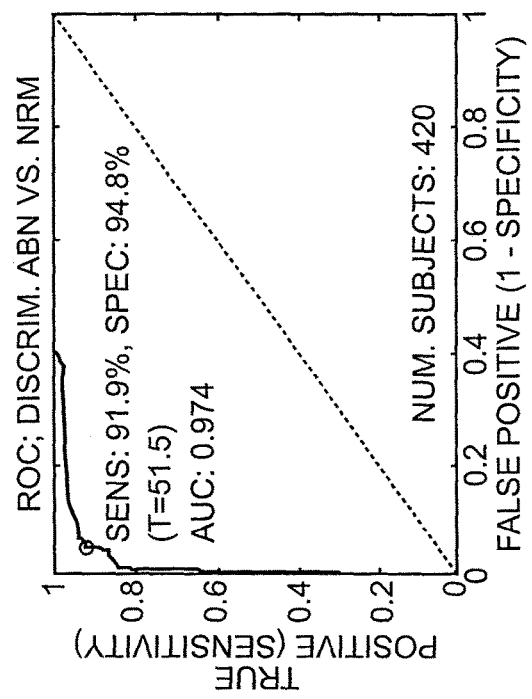
FIG. 4A
FIG. 4B
FIG. 4C

DEVELOPMENT OF FULLY-AUTOMATED CLASSIFIER BUILDERS FOR NEURODIAGNOSTIC APPLICATIONS

The present invention relates to the field of neurological evaluation, and specifically, to classification systems for evaluation of electrical brain activity.

All of the brain's activities, whether sensory, cognitive, emotional, autonomic, or motor function, is electrical in nature. Through a series of electro-chemical reactions, mediated by molecules called neurotransmitters, electrical potentials are generated and transmitted throughout the brain, traveling continuously between and among the myriad of neurons. This activity establishes the basic electrical signatures of the electroencephalogram (EEG) and creates identifiable frequencies which have a basis in anatomic structure and function. Understanding these basic rhythms and their significance makes it possible to characterize the electrical brain signals as being within or beyond normal limits. At this basic level, the electrical signals serve as a signature for both normal and abnormal brain function, and an abnormal brain wave pattern can be a strong indication of certain brain pathologies.

Currently, electrical brain activity data is collected and analyzed by an EEG technician, and is then presented to a neurologist for interpretation and clinical assessment. This makes the currently available EEG equipment inadequate for neuro-triage applications in emergency rooms or at other point-of-care settings. Thus, there is an immediate need for real-time objective evaluation of electrical brain signals in order to enable clinicians, EMTs or ER personnel, who are not well trained in neurodiagnostics, to easily interpret and draw diagnostic inferences from the data recorded at the point-of-care. This in turn will help the medical personnel in selecting an immediate course of action, prioritizing patients for imaging, or determining if immediate referral to a neurologist or neurosurgeon is required.

Objective assessment of electrical brain signals may be performed using a classifier that provides a mathematical function for mapping (or classifying) the recorded data into one or more predefined diagnostic classes or categories. Classifiers are built by forming a training dataset, where each subject is assigned a "label," namely a diagnostic class based on information provided by doctors with the help of state-of-the-art diagnostic systems, such as CT scan, MRI, etc. (these labels are usually referred to as "gold standard" labels). For each subject in the same dataset, a large set of quantitative signal attributes or features is also available. The training dataset is used for training a classifier to distinguish between one or other diagnostic categories. The process of building a classifier from a training dataset involves the selection of a subset of features (from the set of all quantitative features), along with the construction of a mathematical function which uses these features as input and which produces as its output an assignment of the subject's data to a specific class. After a classifier is built, it may be used to classify unlabeled data records as belonging to one or the other potential diagnostic classes. Classification accuracy is then reported using a testing dataset that does not overlap with the training set, but for which gold standard classification data is also available. The accuracy of the classifier is dependent upon the selection of features that comprise part of the specification of the classifier. Well-chosen features may not only improve the classification accuracy, but also reduce the amount and quality of training data items needed to achieve a desired level of classification performance. However, the task of finding the "best" features may require an exhaustive search of all possible combinations of features, and computation and evaluation of each possible classifier. For example, finding the overall best combination of K features from among N available features (where N is typically much larger than K, denote herein by N>>K) would require the computation and evaluation of C(N, K) classifiers (the number of all possible selections of K features taken from a pool of N features), where:

$$C(N, K) = \frac{N!}{(N-K)!K!}$$

For a significantly large value of N, an exhaustive search of the best combination of features would be a very time-consuming and computationally-intensive task. Therefore, most classification systems currently rely heavily on the art and experience of the (human) designer of the classifier for selecting the features that go into the classifier, which can be time-intensive, and can also result in subjectivity, missed solutions that may be better at classifying, and which can additionally be prone to human error.

The present disclosure provides fully-automated methods for constructing classifiers for the task of classifying subjects based on a set of quantitative features derived from electrical brain signals.

One aspect of the present disclosure includes a method of building, in an automated fashion, one or more binary classifiers for the purpose of classifying subjects using a set of features derived from the electrical signals produced by their brain. The method comprises the steps of acquiring quantitative signal features from a reference database, and organizing the quantitative features into hierarchical classes based on one or more quantitative measures indicative of the performance of the features. A set of features is then selected at random from the highest class in the hierarchical organization. The set of features is encoded into at least one bit string, and one or more evolutionary algorithms are then applied to the bit string in order to arrive at a classifier with excellent performance.

Another aspect of the present disclosure includes a method of building a Linear Discriminant Function for classification of electrical brain signals. The method comprises the steps of selecting multiple sets of quantitative features from a larger available pool of features derived from electrical brain activity data, forming a population of possible initial solutions, called "chromosomes," using the selected sets of features, and applying genetic algorithm operators to the population of chromosomes.

Yet another aspect of the present disclosure includes a method of building a Linear Discriminant Function for classification of electrical brain signals. The method comprises the steps of selecting a set of quantitative features from a larger available pool of features derived from electrical brain activity data, encoding a chromosome as a binary bit string using the selected set of features, inverting the value of at least one bit at a random location on the bit string to generate a new bit string, and computing an objective function value of the new bit string.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the various aspects of the invention.

BRIEF DESCRIPTION OF DRAWINGS

FIG. 3A shows the evolution of the average value of objective function of candidate solutions using a genetic algorithm, as described in Example 1;

FIG. 3B shows the evolution of the highest value of objective function of candidate solutions using a genetic algorithm, as described in Example 1;

FIG. 3C shows the evolution of the number of features of candidate solutions using a genetic algorithm, as described in Example 1;

FIG. 4A shows the evolution of the objective function value of a candidate solution using a combination of a genetic algorithm and the Modified Random Mutation Hill Climbing algorithm, as described in Example 2;

FIG. 4B shows the ROC curve for the Linear Discriminant Function obtained using a combination of a genetic algorithm and the Modified Random Mutation Hill Climbing algorithm, as described in Example 2;

FIG. 4C illustrates the distribution of discriminant outputs (scores) for a Linear Discriminant Function obtained using a combination of a genetic algorithm and the Modified Random Mutation Hill Climbing algorithm, as described in Example 2.

DESCRIPTION OF EXEMPLARY EMBODIMENTS

Figure 1A:
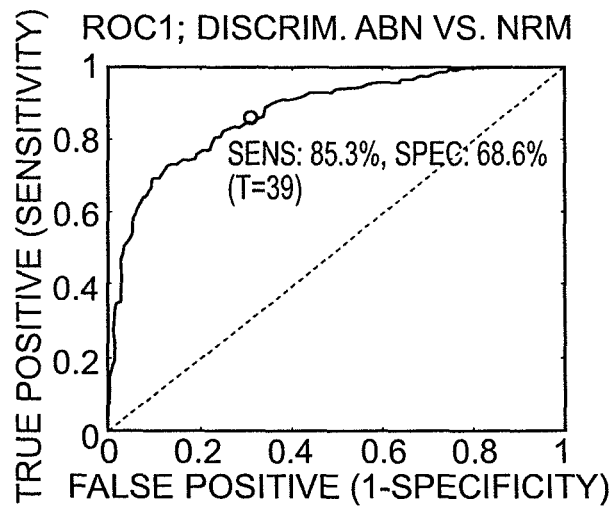
FIGS. 1A and 1B illustrate the performance (ROC curve) of a normal/abnormal classifier for a sample group of 396 subjects.

Reference will now be made in detail to certain embodiments consistent with the present disclosure, examples of which are illustrated in the accompanying drawings. Wherever possible, the same reference numbers will be used throughout the drawings to refer to the same or like parts.

In an exemplary embodiment, data corresponding to electrical brain activity is used to assess the brain function of a subject. The electrical brain signals are measured and analyzed at the point-of-care using a portable brain-state assessment device developed using Bx™ technology. A brain-state assessment device for acquiring and processing electrical brain signals is described in commonly-owned U.S. application Ser. No. 12/361,174, which is incorporated herein in its entirety.

In an exemplary embodiment of the Bx™ technology, a subject's electrical brain activity is recorded using a varying number of non-invasive electrodes located at standardized positions on the scalp and forehead, and the subject's brain electrical signals are assessed with reference to one or more databases. For example, collected normative data, indicative of normal brain electrical activity, is used to establish quantitative features which clearly distinguish brain signals produced in the presence and absence of brain disorders. This normative dataset includes brain activity data of a control group or population comprising of individuals similar to the subject in one or more aspects, such as age, gender, etc. The collected normative database employed by the inventor has been shown to be independent of racial background and to have extremely high test-retest reliability, specificity (low false positive rate) and sensitivity (low false negative rate).

The data corresponding to the acquired electrical brain signals are processed in a digital signal processor, which is configured to perform the following tasks:

a) Automatic identification and removal of several types of non brain-generated artifacts from the acquired brain electrical signal data;

b) Extraction of quantitative signal features; and c) Classification based on Linear Discriminant Analysis (LDA), using pre-selected subsets of age-normalized features (Z-scores).

The exemplary processor is configured to implement a denoising algorithm to identify data that is contaminated by non brain-generated artifacts, such as eye movements, electromyographic activity (EMG) produced by muscle tension, spike (impulse), external noise, etc. The artifact-free data is then processed to extract signal features and classify the extracted features to provide an assessment of brain function.

By way of example, the feature extraction algorithm can take as input a number of "artifact-free" or "denoised" data epochs having a temporal length of 2.56 seconds, which corresponds to 256 samples for data sampled at 100 Hz. In an exemplary embodiment, the processor is configured to perform a linear feature extraction algorithm based on Fast Fourier Transform (FFT) and power spectral analysis, according to a method disclosed in commonly-assigned U.S. patent application Ser. Nos. 11/195,001 and 12/041,106, which are incorporated herein by reference in their entirety. In short, the algorithm computes quantitative features obtained using the Fast Fourier Transform (FFT), and calculating the spectral power at predefined frequency bands and other signal features. The frequency composition can be analyzed by dividing the signal into the traditional frequency bands: delta (1.5-3.5 Hz), theta (3.5-7.5 Hz), alpha (7.5-12.5 Hz), beta (12.5-25 Hz), and gamma (25-50 Hz). Higher frequencies, up to and beyond 1000 Hz may also be used. Univariate features are computed by calculating the absolute and relative power for each of the electrodes or between a pair of electrodes within selected frequency bands, and the asymmetry and coherence relationships among these spectral measurements within and between the sets of electrodes. The processor may also be configured to compute multivariate features, which are non-linear functions of groups of the univariate features involving two or more electrodes or multiple frequency bands. The computed measures are normalized by performing age-regression and Z-transformation to obtain features (Z-scores) for discriminant analysis.

In another embodiment, the processor is configured to perform a linear feature extraction algorithm based on wavelet transforms, such as Discrete Wavelet Transform (DWT) or Complex Wavelet Transforms (CWT). In yet another embodiment, the processor is configured to perform feature extraction using non-linear signal transform methods, such as wavelet packet transform, according to a method disclosed in commonly-assigned U.S. patent application Ser. No. 12/361,174, which is incorporated herein by reference in its entirety. The features extracted by this method are referred to as Local Discriminant Basis (LDB) features.

In another embodiment consistent with the present disclosure, diffusion geometric analysis is used to extract non-linear features according to a method disclosed in commonly-assigned U.S. patent application Ser. No. 12/105,439, which is incorporated herein by reference in its entirety.

The extracted signal features (such as the diffusion geometry features, Local Discriminant Basis features, FFT features, etc.) are classified into brain-state categories using a classification algorithm, such as Linear Discriminant Analysis (LDA). All the extracted features are age-regressed and Z-transformed for discriminant analysis. The LDA optimally combines the features (Z-scores) into a discriminant output/score that possesses the maximum discriminating power. In one embodiment, the discriminant analysis used is a two-category linear classifier (also called "dichotomizer" or "binary test") which assigns for each given subject a discriminant score (a real-valued number) between 0 and 100. The classification rule which is commonly associated with Linear Discriminant Functions (LDF) is the following: after a cut-off threshold T is selected (for example, but not necessarily, in the middle of the discriminate score range i.e. T=50), the classifier assigns any subject with a discriminant score g≤T to the category "brain state A" and assigns any subject with a score g>T to the category "brain state B." A score "lower than or equal to 50" indicates that the subject is more likely to belong to brain state A than to brain state B, and vice versa. Examples of different classification classes include, but are not limited to, "normal brain function" vs. "abnormal brain function", "organic brain dysfunction" vs. "functional brain dysfunction", "focal brain dysfunction" vs. "diffuse brain dysfunction", "normal brain function" vs. "(closed-head) traumatic brain injury (TBI)," "normal brain function" vs. "mild TBI (concussion)", etc. The discriminant scores, $g_A$ and $g_B$ corresponding to classes A and B, are computed for any subject with the following Fisher LDF formulas:

$$g_A=100.G(1)/(G(1)+G(2)), g_B=100.G(2)/(G(1)+G(2))$$

$$G(1)=\exp(Z.W_A+C_A), G(2)=\exp(Z.W_B+C_B)$$

where Z denote the vector of age-regressed z-transformed features computed for any subject. Since $g_B=100-g_A$, only $g_A$ may be referred to as the "discriminant output/score" and simply denoted by g (or g(Z) to emphasize that it is a function of the vector of Z-transformed features). $W_A$ and $W_B$ denote two weight vectors that are derived from a reference database of training data (training set), and $C_A$ and $C_B$ are two constants which are commonly called bias or threshold weights, also derived from the same training data. The weights for the different monopolar and/or bipolar univariate and multivariate features may be estimated from quantitative signal features (e.g., age-regressed Z-scores) that are stored in a population reference database. The quantitative signal features comprise a variety of linear and non-linear features, including but not limited to, diffusion geometry features, Local Discriminant Basis features, FFT features, etc. In one embodiment, the population reference database comprises population normative data indicative of brain electrical activity of a first plurality of individuals having normal brain state, or population reference data indicative of brain electrical activity of a second plurality of individuals having an abnormal brain state. In another embodiment, the weights are selected from a database of the subjects own brain electrical activity data generated in the absence or presence of an abnormal brain state. The weights and constants entirely define the Linear Discriminant Function and are pre-selected using a training routine such that they result in the "best" separation between the classes. Therefore, the design or construction of a Linear Discriminant Function targeting any classification task (e.g. "Normal" vs. "Abnormal" brain function) requires selection of a set of quantitative signal features K from a large available pool of features N (where N>>K). The selection of the "best" features results in the "best" classification performance, characterized by, for example, the highest sensitivity/specificity and lowest classification error rates.

In an exemplary embodiment, the search for the "best" features for a binary classification task is performed using a fully-automated system (hereinafter "classifier builder"), implemented as a computer program, the output of which is a Linear Discriminant Function classifier. Identification of the "best" features for a particular classification task is performed by computing multiple classifiers using different combination of features, and evaluating each possible classifier using an "objective function" that is directly related to classification performance.

Figure 1B:
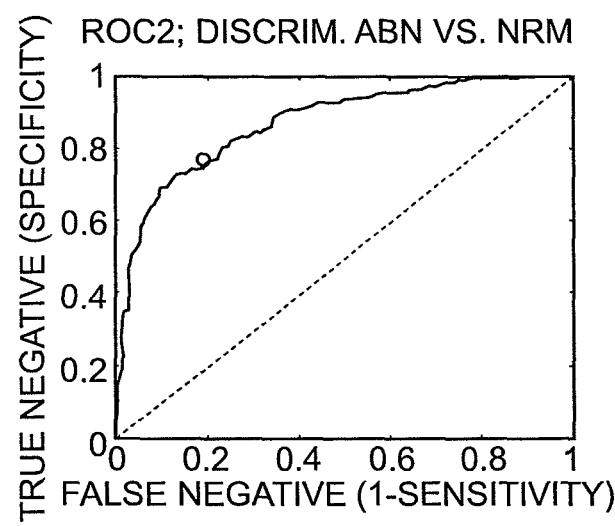
Figure 1C:
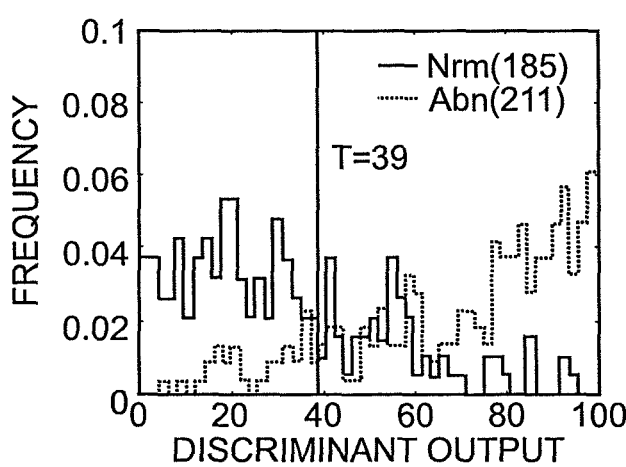
FIG. 1C illustrates the distribution of discriminant outputs (scores) for a classifier of brain function (Normal brain function ("normal") vs. Abnormal brain function ("abnormal")), for a sample group of 396 subjects.

In one embodiment, the objective function is the area under the Receiver Operating Characteristics (ROC) curve of a Linear Discriminant Function, which is usually referred to as "Area Under the Curve" (AUC). The ROC curve is widely used in various applications of engineering and medicine to illustrate quantitatively the performance of a binary classification system such as a binary Linear Discriminant Function. For a given linear discriminant-based classifier, e.g. of normal/abnormal brain function, the ROC curve indicates the sensitivity and specificity that can be expected from this particular classifier at different values of the classification threshold T. For a "Normal" vs. "Abnormal" discriminant, "Normal" may be referred to as "disease absent" and "Abnormal" as "disease present". Using this convention, sensitivity of the classifier is defined as the ratio of "true positives" over the number of subjects in the sample group for whom "disease" is present. Specificity of the classifier is defined as the ratio of "true negatives" over the number of subjects in the sample group for whom "disease" is absent. As described earlier, the output of a Linear Discriminant Function is a number g(Z) that can take any value between 0 and 100. Once a critical value (or threshold) T is selected, the output of the test becomes binary, and sensitivity and specificity for that particular threshold can be calculated. The ROC is the curve through the set of points: {(1−specificity(T), sensitivity(T))}, which is obtained by varying the value of the threshold T in fixed increments between 0 and 100. FIGS. 1A-1C illustrate ROC curves and histogram of discriminant scores for a normal/abnormal classifier comprising a sample group of 396 subjects. The abnormal group of 211 subjects comprised individuals suffering from vascular dementia, encephalopathies, head injury, and several other abnormal brain conditions. As shown in the FIGS. 1A and 1B, the ROC curves illustrate the achievable statistical performance of the normal/abnormal classifier for a threshold value T=39. The threshold T=39 was selected to achieve the highest sensitivity and specificity for the classification.

After the ROC curve is obtained, the area under the ROC curve (AUC) is calculated, which represents the surface area of the region located under the ROC curve. AUC is a single number between 0 and 1, which reflects, jointly, the sensitivity and specificity of a binary classifier. Thus, AUC provides a quantitative global measure of achievable classifier performance. It is generally considered that a classifier with an AUC≥0.95 exhibits 'excellent' classification performance, and a classifier with 0.90≤AUC≤0.95 exhibits 'good' classification performance.

Figure 2:
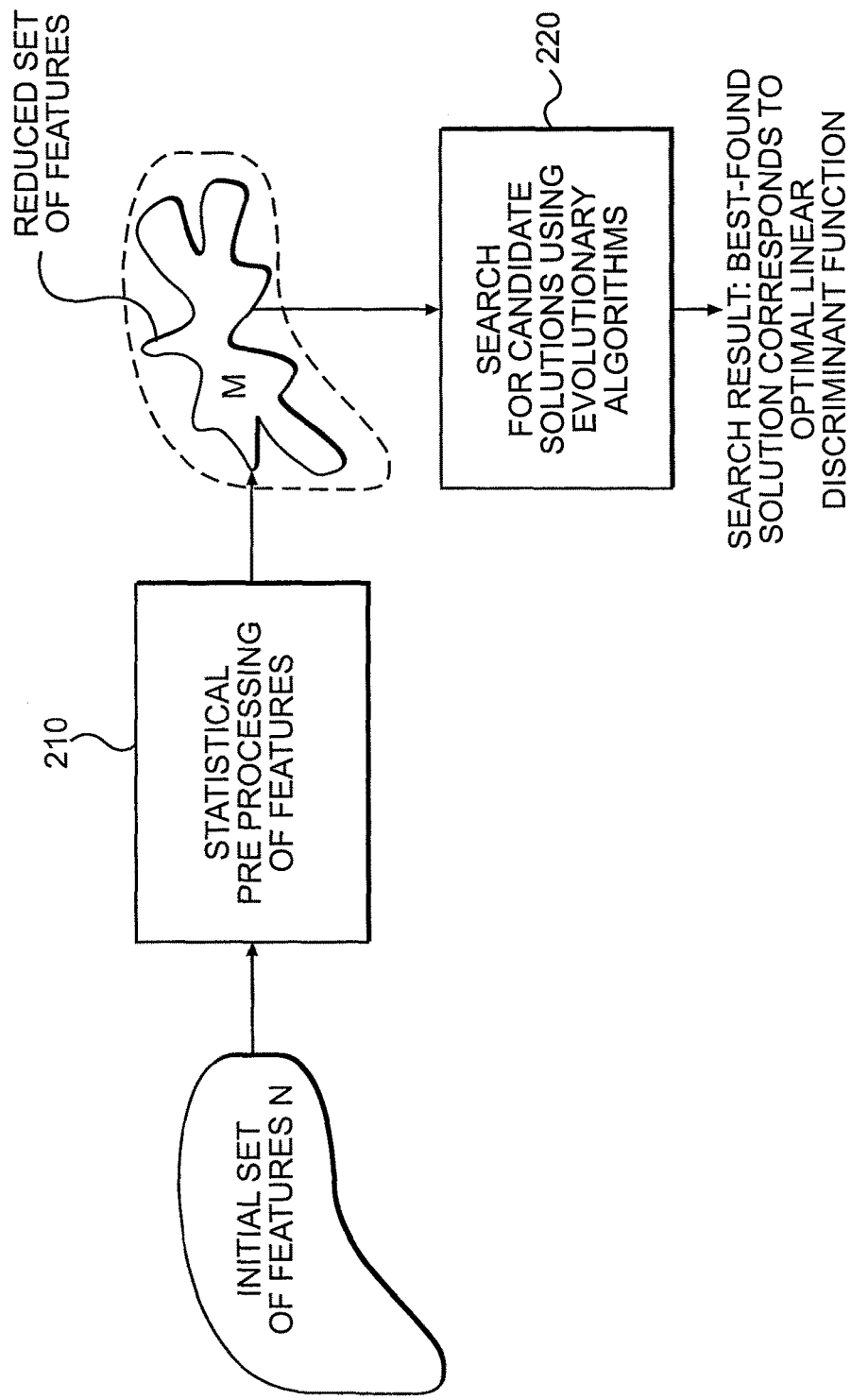
FIG. 2 illustrates a method of constructing a fully-automated classifier builder.

FIG. 2 illustrates a method of constructing a fully-automated classifier builder according to some embodiments of the present disclosure. The first step is the statistical pre-processing of all available features (step 210). In one embodiment, each available feature is associated with two quantitative properties: replicability (RE) and discriminative power (DP). Replicability is a quantitative measure of the ability of a feature to maintain a stable value across successive measurements of electrical brain signals. Discriminative power is a measure of the ability of a feature to classify a group of data. Features with the highest RE and DP values result in a Linear Discriminant Function with the "best" classification performance. In one exemplary embodiment, feature replicability RE is quantified using a database of subjects for which the pool of features are computed twice, during a first time period $t_1$ and during a second time period $t_2$, immediately following $t_1$. The replicability of any feature f is derived from the mean value of the magnitude of the difference between the two instances of this feature during time periods $t_1$ and $t_2$. In one exemplary embodiment, feature discrimination power DP is quantified using a training database of features for two classes of subjects, for example: normal and abnormal. The DP of feature f is computed as the magnitude of the scalar ratio of the difference of the mean values of f over the two classes divided by the average of the two standard deviations of feature f over the two classes, i.e., $$DP=abs(m1-m2)/((\sigma 1+\sigma 2)/2)$$

where m1 is the mean value of feature f over the class of normal subjects, σ1 is the standard deviation of feature f over the class of normal subjects, m2 is the mean value of feature f over the class of abnormal subjects, σ2 is the standard deviation of feature f over the class of abnormal subjects.

In one exemplary embodiment, the preprocessing step involves the organization (grouping) of a pool of N features into four classes (class 1, class 2, class 3 and class 4) based on their RE and DP values, with class 1 comprising the features with the highest RE, DP values and class 4 comprising the features with the lowest RE, DP values. This hierarchical organization of features facilitates the initial selection of a group of M features from the pool of N available features.

Referring again to FIG. 2, the next step is the search for candidate solutions (Linear Discriminant Functions) from the group of M features using one or more evolutionary algorithms (step 220). In one embodiment, the evolutionary algorithm used is a genetic algorithm (GA). GA is a meta-heuristic algorithm working with a population of solutions encoded into chromosomes and each characterized by a objective function value, which returns a quantitative measure of their "goodness" (where "goodness" of a chromosome is directly related to the performance of the classifier defined by the chromosome). In the context of the present disclosure, a chromosome represents a subset of K features from the pool of M features. A chromosome comprises a binary M-integer string, where K bits are set to 1 and all other bits are set to 0. According to this representation, the individual bits in the string correspond to the genes of the chromosome. A population of P initial chromosomes is generated through random selection of K features from the pool of M features, repeated P times. Evolution of the population, that is, improvement of the "average value of objective function" of the population is performed by repeatedly using one or more GA operators, for example, ranking, selection, crossover, mutation, etc. In one exemplary embodiment, the size of the population is kept constant from one generation to the next, namely a population of P parent chromosomes gives rise to P offspring. During the evolution process, some features are preserved and others are removed from the individual chromosomes, which results in a set of close-to-optimal chromosomes, each chromosome containing K bits set to 1. (Note that K is not a constant so that the number of features comprised in a chromosome need not be the same for each chromosome of any given population during the evolution process). Each GA chromosome represents a candidate solution to the problem of finding the "best" Linear Discriminant Function for a particular classification task.

As noted earlier, the evolution of the population of chromosomes is carried out using several GA operators. In one embodiment, the first operator applied is the ranking. Ranking is performed by computing the value of the objective function for each chromosome in the population, and assigning a fitness value to each chromosome depending on this value of the objective function. The fitness value is then used by GA to mark the performance of a single chromosome during the algorithm execution. This value corresponds to the objective function value, which means that the chromosome with the highest fitness value, also has highest value of objective function and vice versa. In one exemplary embodiment, the objective function is the AUC (Area Under the ROC Curve) of a classifier built from the K features of a particular chromosome.

In one embodiment, the second operator applied is selection, which selects individual pairs of chromosomes for breeding, depending on their objective function values. A whole new population of possible solutions is produced by selecting the best individuals from the current generation, and "mating them" to produce a new set of individuals. By favoring the mating of the more fit individuals, the most promising areas of the search space are explored.

In one such embodiment, the individual chromosomes are selected using a roulette wheel selection method, which is based on the stipulation that the fittest individuals have a greater chance of survival than weaker ones. This replicates nature in that fitter individuals will tend to have a better probability of survival and will go forward to form the mating pool for the next generation. The roulette wheel selection method proceeds by assigning the largest share of the roulette wheel to the fittest individual chromosome (the chromosome with the highest ranking), and the weakest chromosome (the chromosome with the lowest ranking) gets the smallest share of the wheel. The number of times the roulette wheel is spun is equal to the size of the population. Each time the wheel is spun, the fitter individuals have the greatest chance of being selected for the next generation and subsequent mating pool.

In another embodiment, the individual chromosomes are selected using a stochastic universal sampling method, where the population is laid out in a random order as in a pie graph, and each individual in the population is assigned space on the pie graph in proportion to their objective function value. An outer roulette wheel is placed around the pie with N equally-spaced pointers, where N is equal to the number of individuals to be selected for breeding. A single spin of the roulette wheel then simultaneously selects all N members of the mating pool.

In certain embodiments, a crossover (recombination) operator is applied to the parent chromosomes, which recombines (exchanges) parts of the individual chromosomes and creates two offspring chromosomes. In one embodiment, a single-point crossover operator is applied, wherein the crossover between the parent chromosomes occur at just one bit position. In another embodiment, a multi-point crossover operator is applied, which allows the crossover between the parent chromosomes to occur at multiple locations. In yet another embodiment, a reduce-surrogate crossover operator is applied, which restricts the location of crossover points and allows crossover to occur only where the value of the bit differs.

In some embodiments, a mutation operator is applied to individual chromosomes obtained from the crossover operator. The mutation operator changes the value of a single bit from 1 to 0, and vice versa, at a randomly chosen position in the chromosome string.

In various embodiments, once the offspring is produced by selection, recombination and mutation of individuals from the old population, the objective function value of the offspring is determined. If the number of offspring produced is less than the size of the original population, the new population can be created as a combination of chromosomes from the offspring and from the original population. Similarly, if not all offspring are to be used at each generation or if more offspring are generated than the size of the old population, then a reinsertion scheme is used to determine which individuals are to exist in the new population. In one such embodiment, a objective function value-based reinsertion scheme is used, where only the best offspring are reinserted into the population. In another embodiment, if less offspring than parents are produced, an elitist scheme is used where the worst parents are replaced by the offspring. The reinsertion scheme ensures that the best individuals are preserved for many generations; however, with every generation some new individuals are inserted.

Through the application of one or more GA operators, as disclosed above, a new population of chromosomes is created in each generation. The new generation contains a higher proportion of the characteristics possessed by the "good" members of the previous generation. In this way, over many generations, the population evolves and "good" characteristics are spread throughout the population.

As the algorithm proceeds through multiple generations, the objective function value of the best and the average chromosome in each generation increases towards a global optimum. In some embodiments, the population converges at the end of the algorithm, i.e., the average value of objective function of the population approaches that of the best chromosome. In some embodiments, the algorithm is stopped after a predetermined value of the objective function for a "high-performing" chromosome is obtained, or if a desired average objective function is achieved. In another embodiment, the algorithm is stopped after a specific number of generations have been produced, which is equivalent to a predetermined maximum algorithm run time. The population of chromosomes in the final generation represents a set of solutions to the problem of finding the most optimal classifier.

In yet another exemplary embodiment, the objective function, previously defined as the AUC of the classifier ROC, is modified by subtracting a "cost" which is chosen as an increasing function of the number of features in the classifier (number of ones in the chromosome representation). This results in reducing the growth rate of the number of discriminant features across successive generations.

In another exemplary embodiment, which can be used in a stand-alone fashion or can be combined with the GA algorithm (for example, as a final "local search" after a GA-based solution has been produced), the search for candidate solutions is performed using Random Mutation Hill-Climbing (RMHC) method. The RMHC algorithm uses only the evolutionary operation of mutation, but makes no use of crossover, as in the GA algorithm. The first step in RMHC implementation is the random selection of a chromosome comprising a binary M-integer string, where K bits are set to 1 and all other bits are set to 0. K corresponds to the initial set of discriminant features for a particular LDF. The value of a single bit is then flipped at a randomly chosen position in the chromosome string. The objective function value of the resultant string is computed and compared to the objective function value of the previous string. In one such embodiment, the area under the ROC curve (AUC) is used for objective function evaluation. If the changed bit value leads to an equal or higher objective function value, then the resultant string becomes the current string. A bit value of this new current string is changed at a random location, and the process is continued until an optimum string is obtained or until a maximum number of objective function evaluations is performed. The final string generated represents the "best" solution to the problem of finding a locally optimal LDF.

In another exemplary embodiment, the search for candidate solutions is performed using a modified Random Mutation Hill-Climbing (mRMHC) method, where the values of two bits (instead of one) are inverted at two randomly selected locations on the chromosome string. An initial string is selected where K bits are set to one and the others are set to zero. One of the bits of the current string that was set to zero, selected at random, is changed to 1, and similarly, one of the bits that was set to 1 is changed to 0. This preserves the total number of discriminant features (the number of ones in the string) throughout the algorithm runtime. The final string generated represents the "best" solution to the problem of finding a locally optimal LDF, under the constraint of a constant number of features in the solution.

In yet another exemplary embodiment, the search for candidate solutions is performed by combining the genetic algorithm and the mRMHC algorithm into a single classifier-builder algorithm. The best solution obtained from the genetic algorithm is selected for the application of mRHMC.

The following examples are provided to better explain the various embodiments and should not be interpreted in any way to limit the scope of the present disclosure.

Figure 3E:
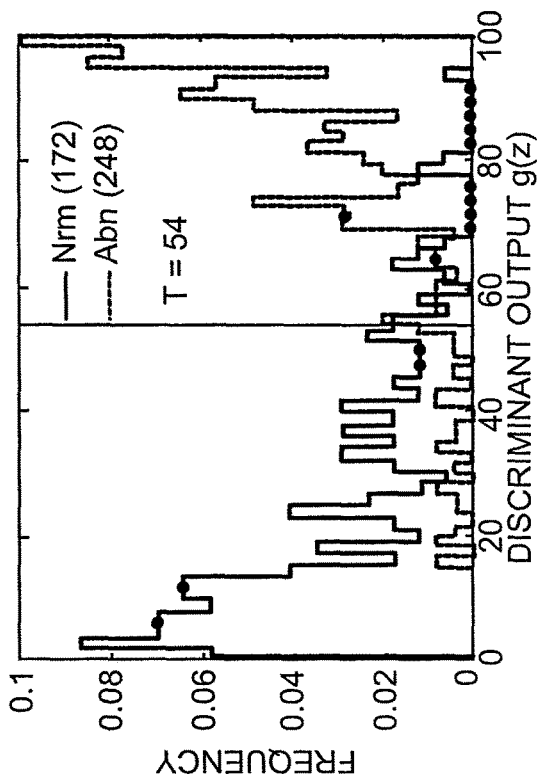
FIG. 3E illustrates the distribution of discriminant outputs (scores) for a Linear Discriminant Function with the overall highest value of objective function, as described in Example 1.
Figure 3D:
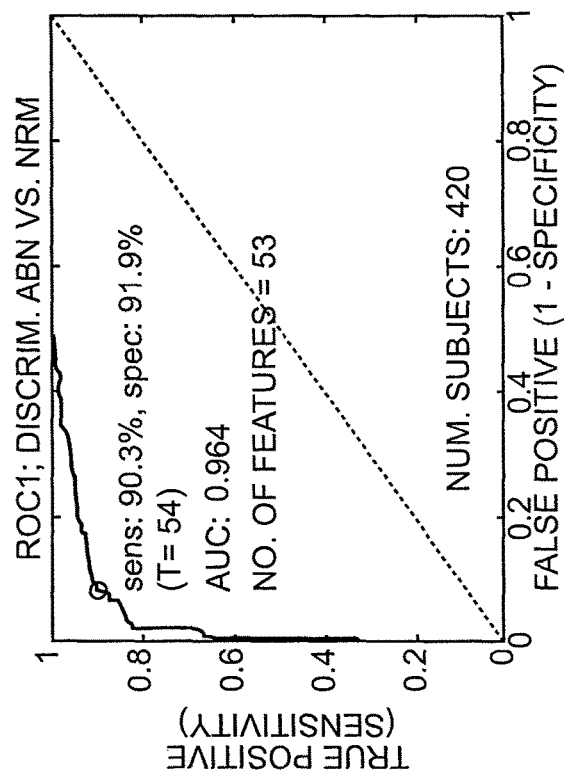
FIG. 3D shows the ROC curve for the Linear Discriminant Function with the overall highest value of objective function, as described in Example 1.

Example 1. Application of GA to Automatic Building of "Normal Brain Function" vs. "Abnormal Brain Function" Classifier Genetic algorithm was applied for building a "Normal" vs. "Abnormal" Linear Discriminant Function. Statistical preprocessing of an initial pool of 876 quantitative scalar features, computed from electrical brain activity recordings (EEG), resulted in 301 class 1 features (i.e. features with the highest values of Replicability and Discriminative Power). A population of initial chromosomes was generated through random selection of features from the pool of 301 features. Evolution of the population, that is, improvement of the objective function value of the solutions was performed by using one or more GA operators. The overall performance measure of the chromosomes was evaluated using AUC as an objective function. FIGS. 3A-3C shows the evolution of the average value of objective function, the highest value of objective function and the number of features of the candidate solutions over sixty generations. The algorithm produced several excellent solutions (classifiers), and the highest value of objective function obtained was 0.964. FIGS. 3D and 3E show the ROC curve for the Linear Discriminant Function with the overall highest value of objective function. The initial number of features used in this solution was 53. Both the sensitivity and the specificity was higher than 90% for this solution.

Example 2. Application of a Combined GA and mRMHC Algorithm to Automatic Building of "Normal Brain Function" vs. "Abnormal Brain Function" Classifier Both genetic algorithm and mRMHC were applied for building a "Normal" vs. "Abnormal" Linear Discriminant Function. Statistical preprocessing of an initial pool of 876 discriminant features resulted in 301 class 1 features. Application of GA to the initial pool of features resulted in several solutions (Linear Discriminant Functions) with high objective function values. The solution with the highest value of objective function was then selected for mRMHC implementation. The number of features used in this solution was 53. FIG. 4A shows the evolution of objective function value as a function of iteration number. The maximum number of iterations was set at 2250. The best solution obtained had an objective function value of 0.974, and the number of features in each candidate solution remained constant throughout the run. FIGS. 4B and 4C show the ROC curve and the distribution of discriminate scores, respectively, for the Linear Discriminant Function with the overall highest value of objective function. The sensitivity was higher than 91% and the specificity was higher than 94% for this solution.

Embodiments consistent with the present disclosure, using the fully-automated classifier builders and stored data of the brain activity of thousands of subjects having different neurological indications, may provide a rapid and accurate assessment of the brain state of a subject. The classifier-building algorithms may be executed by a processor capable of integration in a standalone computer system or a portable handheld device. In one embodiment, the solutions obtained from the classifier-builders are stored in a portable handheld device used for point-of-care assessment of electrical brain signals. Detailed description of such portable handheld devices is provided in commonly-owned U.S. application Ser. No. 12/361,174, which is incorporated herein by reference in its entirety. In another embodiment, the solutions obtained from the classifier-builders are accessed wirelessly or through a wired connection from a remote computer system or data storage device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of building a linear discriminant function for classification of brain electrical activity data into diagnostic categories, the method comprising:
   providing a data storage device comprising a reference database of brain electrical activity data and a processor;
   acquiring with the processor quantitative brain electrical activity features from the brain electrical activity data in the reference database;
   calculating with the processor one or more quantitative measures for each of the acquired quantitative features, the one or more quantitative measures being indicative of classification performance of the acquired quantitative features;
   selecting with the processor a reduced pool of brain electrical activity features from the acquired quantitative features based on the one or more quantitative measures associated with each of the acquired quantitative features, wherein calculation of the one or more quantitative measures and selection of the reduced pool of features is performed prior to the application of a genetic algorithm;
   selecting with the processor multiple subsets of quantitative brain electrical activity features from the reduced pool of features;
   forming with the processor an initial population of chromosomes, each chromosome of the initial population including one of the selected subsets of features and representing a linear discriminant function for classification of brain electrical activity data into diagnostic categories;
   applying with the processor genetic algorithm operators to the initial population of chromosomes to derive a new population of chromosomes, wherein each individual chromosome in the new population of chromosomes includes a subset of the brain electrical activity features that is generated from the subsets of features of the initial population of chromosomes;
   determining objective function values of the chromosomes in the new population;
   repeating the applying step and the determining step until the objective function value of one of the chromosomes in the new population is above a predetermined threshold; and
   storing a final linear discriminant function on non-volatile media for use in classification of brain electrical activity data into the diagnostic categories, wherein the stored final linear discriminant function is defined by the subset of brain electrical activity features of the chromosome having the objective function value above the predetermined threshold.

2. The method of claim 1, wherein an individual chromosome in the initial population of chromosomes is encoded as a binary bit string.

3. The method of claim 1, further comprising evaluating with the processor a performance measure of each individual chromosome in the initial population of chromosomes using an objective function.

4. The method of claim 3, wherein the objective function is Area Under the Receiver Operating Curve of a Linear Discriminant Function.

5. The method of claim 1, wherein the initial population of chromosomes evolves through multiple generations through application of the genetic algorithm operators.

6. The method of claim 1, wherein the genetic algorithm operators comprise a selection operator.

7. The method of claim 1, wherein the genetic algorithm operators comprise a crossover operator.

8. The method of claim 1, wherein the genetic algorithm operators comprise a mutation operator.

9. The method of claim 1, wherein a Modified Random Mutation Hill Climbing algorithm is applied to a high performing chromosome obtained through the application of the genetic algorithm operators.

10. The method of claim 1, wherein the final linear discriminant function is a Linear Discriminant Function for classification of brain electrical activity data into diagnostic categories that include at least one of: (i) normal brain function, (ii) abnormal brain function, (iii) organic brain dysfunction, (iv) functional brain dysfunction, (v) focal brain dysfunction, (vi) diffuse brain dysfunction, (v) (closed-head) traumatic brain injury (TBI), and (vi) mild TBI (concussion).

11. A method of building a linear discriminant function for classification of brain electrical activity data into diagnostic categories, the method comprising:
providing a data storage device comprising a reference database of brain electrical activity data and a processor;
acquiring with the processor quantitative brain electrical activity features from the brain electrical activity data in the reference database;
calculating with the processor one or more quantitative measures for each of the acquired quantitative features, the one or more quantitative measures being indicative of classification performance of the acquired quantitative features;
selecting with the processor a reduced pool of brain electrical activity features from the acquired quantitative features based on the one or more quantitative measures associated with the acquired quantitative features, wherein calculation of the one or more quantitative measures and selection of the reduced pool of features is performed prior to the application of an evolutionary algorithm;
selecting with the processor a set of quantitative brain electrical activity features from the reduced pool of features;
encoding with the processor a chromosome as a binary bit string including a bit corresponding to each feature in the reduced pool of features, wherein the bits in the binary bit string corresponding to the selected set of features are set in an active state and the remaining bits in the binary bit string are set in an inactive state, wherein the binary bit string represents a linear discriminant function for classification of brain electrical activity data into diagnostic categories;
inverting with the processor at least one bit value at a random location on the binary bit string to generate a new binary bit string, wherein inverting the at least one bit value includes switching the at least one bit value from one of the active and inactive states to the other of the active and inactive states;
computing with the processor an objective function value of the new binary bit string;
repeating the steps of inverting the at least one bit value and computing the objective function value until a final binary bit string having an objective function value above a predetermined threshold is obtained; and
storing a final linear discriminant function on non-volatile media for use in classification of brain electrical activity data into the diagnostic categories, wherein the stored final linear discriminant function is defined by the bits in the final binary bit string that are in the active state.

12. The method of claim 11, wherein the objective function is configured to evaluate a performance measure of a binary bit string.

13. The method of claim 11, wherein the objective function is Area Under the Receiver Operating Curve of a Linear Discriminant Function.

14. The method of claim 11, wherein at least two bit values are changed at two random locations on the binary bit string during the inverting step.

15. The method of claim 14, wherein a first bit of the at least two bit values is changed from the active state to the inactive state and a second bit of the at least two bit values is changed from the inactive state to the active state.

16. The method of claim 11, wherein the quantitative features derived from the electrical brain activity data in the reference database include non-linear features.

17. The method of claim 11, wherein the final linear discriminant function is a Linear Discriminant Function for classification of brain electrical activity data into diagnostic categories that include at least one of: (i) normal brain function, (ii) abnormal brain function, (iii) organic brain dysfunction, (iv) functional brain dysfunction, (v) focal brain dysfunction, (vi) diffuse brain dysfunction, (v) (closed-head) traumatic brain injury (TBI), and (vi) mild TBI (concussion).

18. A method of building a binary classifier for classifying brain electrical activity data into diagnostic categories, the method comprising:
providing a data storage device comprising a reference database of brain electrical activity data, wherein the brain electrical activity data is recorded from a plurality of individuals in the presence or absence of brain abnormalities using one or more neurological electrodes;
providing a signal processing device operatively connected to the data storage device, the signal processing device comprising a processor configured to perform the steps of:
acquiring quantitative brain electrical activity features from the brain electrical activity data in the reference database,
calculating one or more quantitative measures for each of the acquired quantitative features, the one or more quantitative measures being indicative of classification performance of the acquired quantitative features,
selecting with the processor a reduced pool of brain electrical activity features from the acquired quantitative features based on the one or more quantitative measures associated with the acquired quantitative features,
selecting multiple subsets of brain electrical activity features from the reduced pool of features,
constructing an initial population of chromosomes, each chromosome of the initial population including one of the selected subsets of features and corresponding to a binary classifier for classification of brain electrical activity data into diagnostic categories,
applying genetic algorithm operators to the initial population of chromosomes to derive a new population of chromosomes, each chromosome in the new population including a subset of the brain electrical activity features that is generated from the subsets of features of the initial population of chromosomes,
determining the classification performance of the chromosomes in the new population using an objective function, and
repeating the applying and determining steps until the classification performance of one of the chromosomes in the new population is above a predetermined threshold; and
storing a final binary classifier for classification of brain electrical activity data into the diagnostic categories on non-volatile media, wherein the stored final binary classifier is defined by the subset of brain electrical activity features of the chromosome having the classification performance above the predetermined threshold.

19. The method of claim 18, wherein the one or more quantitative measures comprises a measure of the replicability of the features.

20. The method of claim 18, wherein the one or more quantitative measures comprises a measure of the discriminative power of the features.

21. The method of claim 18, wherein the final binary classifier is a Linear Discriminant Function for classification of brain electrical activity data into diagnostic categories that include at least one of: (i) normal brain function, (ii) abnormal brain function, (iii) organic brain dysfunction, (iv) functional brain dysfunction, (v) focal brain dysfunction, (vi) diffuse brain dysfunction, (v) (closed-head) traumatic brain injury (TBI), and (vi) mild TBI (concussion).

* * * * *